United States Patent
Okutsu et al.

(10) Patent No.: US 12,123,106 B2
(45) Date of Patent: Oct. 22, 2024

(54) BIOPOLYMER CONCENTRATION METHOD, CRYSTALLIZATION METHOD, AND NANOSTRUCTURED SUBSTRATE

(71) Applicants: NATIONAL UNIVERSITY CORPORATION GUNMA UNIVERSITY, Maebashi (JP); ELECTROPLATING ENGINEERS OF JAPAN LIMITED, Tokyo (JP)

(72) Inventors: Tetsuo Okutsu, Maebashi (JP); Masahiro Ito, Hiratsuka (JP); Akihiro Takura, Hiratsuka (JP)

(73) Assignees: EEJA LTD., Tokyo (JP); NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 354 days.

(21) Appl. No.: 17/601,821

(22) PCT Filed: Apr. 1, 2020

(86) PCT No.: PCT/JP2020/014992
§ 371 (c)(1),
(2) Date: Oct. 6, 2021

(87) PCT Pub. No.: WO2020/217895
PCT Pub. Date: Oct. 29, 2020

(65) Prior Publication Data
US 2022/0178050 A1    Jun. 9, 2022

(30) Foreign Application Priority Data
Apr. 26, 2019  (JP) .................... 2019-085309

(51) Int. Cl.
*C30B 29/58* (2006.01)
*B01J 19/12* (2006.01)
(Continued)

(52) U.S. Cl.
CPC ............ *C30B 29/58* (2013.01); *B01J 19/12* (2013.01); *C07K 1/306* (2013.01); *C30B 7/00* (2013.01); *C30B 30/04* (2013.01); *B82Y 30/00* (2013.01)

(58) Field of Classification Search
CPC .......... B01J 19/12; B82Y 30/00; C07K 1/306; C30B 29/58; C30B 30/00; C30B 30/04; C30B 7/00
See application file for complete search history.

(56) References Cited

U.S. PATENT DOCUMENTS 5,709,943 A * 1/1998 Coleman .............. B01J 20/3293
428/378
9,243,017 B2   1/2016 Aslan
(Continued)

FOREIGN PATENT DOCUMENTS

JP    2003-095800 A    4/2003
JP    2007-230841 A    9/2007
(Continued)

OTHER PUBLICATIONS

PCT/ISA/210, "International Search Report for International Application No. PCT/JP2020/014992," Jun. 30, 2020.
(Continued)

*Primary Examiner* — Hua Qi
(74) *Attorney, Agent, or Firm* — HAUPTMAN HAM, LLP

(57) ABSTRACT

Electromagnetic waves are uniformly distributed on the light-receiving surface side by taking advantage of their property of being easily concentrated in sharp parts, and the front area ($S_A$) on the emission surface side is made larger than the back area ($S_B$) on the light-receiving surface side ($S_A/S_B>1$), thereby forming a more moderate electric field region. A reduced gold fine particle group (average particle size: 20 nm) was self-assembled on a transparent polyester (Continued)

resin film and half-submerged and fixed. This base material was repeatedly immersed in an electroless gold plating solution so that gold particles were deposited on the gold fine particles. 10 microliters of a protein solution was added dropwise to this nanostructured substrate, and crystallized by a hanging drop vapor diffusion method.

6 Claims, 10 Drawing Sheets

(51) Int. Cl.
*C07K 1/30* (2006.01)
*C30B 7/00* (2006.01)
*C30B 30/04* (2006.01)
*B82Y 30/00* (2011.01)

(56) References Cited

U.S. PATENT DOCUMENTS

| | | | |
|---|---|---|---|
| 9,693,423 B2 | 6/2017 | Fukuura | |
| 9,987,610 B2 | 6/2018 | Okutsu | |
| 10,306,774 B2 | 5/2019 | Ito | |
| 2012/0204783 A1 | 8/2012 | Okutsu et al. | |
| 2013/0090459 A1* | 4/2013 | Aslan | C07C 227/42 536/25.4 |
| 2015/0017702 A1* | 1/2015 | Okutsu | C30B 29/58 422/186 |

FOREIGN PATENT DOCUMENTS

| | | |
|---|---|---|
| JP | 2008-137961 A | 6/2008 |
| JP | 2013-010884 A | 1/2013 |
| JP | 5224306 B1 | 7/2013 |
| JP | 2013-177665 A | 9/2013 |
| JP | 2014-172833 A | 9/2014 |
| JP | 2014-530820 A | 11/2014 |
| JP | 2018-048382 A | 3/2018 |
| WO | 2011/030704 A1 | 3/2011 |
| WO | WO-2017169445 A1 * 10/2017 ........... C07C 233/54 |

OTHER PUBLICATIONS

K. L. Wustholz et al., "Structure-Activity Relationships in Gold Nanoparticle Dimers and Trimers for Surface-Enhanced Raman Spectroscopy," Journal of the American Chemical Society, Jul. 21, 2010, p. 10903-10910, vol. 132, No. 31, American Chemical Society.

T. Fukuoka et al., "High Sensitive Analysis Using Surface Enhanced Raman Scattering with Self-assembled Gold Nanoparticles," Journal of Oleo Science, 2014, p. 5-10, vol. 14, No. 1, Japan Oil Chemists Society.

T. Okutsu et al., "Crystallization of membrane protein using the optical alignment effect by surface plasmon resonance of gold nanoparticles," Abstracts of Annual Meeting on Photochemistry, 2017, 1D11.

T. Okutsu, "Crystallization of using the optical alignment effect by surface plasmon resonance of gold nanoparticles," Abstracts of the 98th CSJ Annual Meeting, 2018, 4S7-06.

* cited by examiner

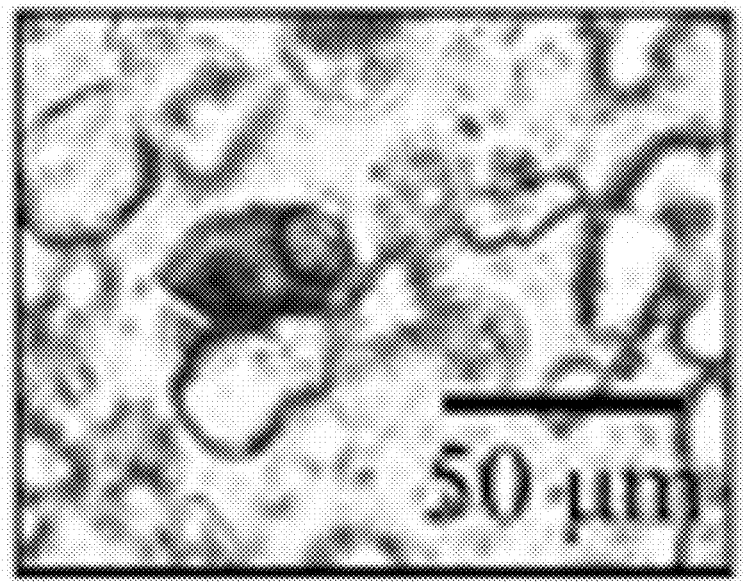
FIG. 10
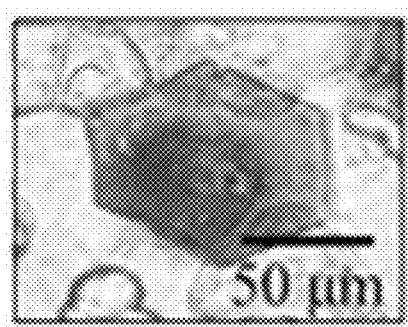 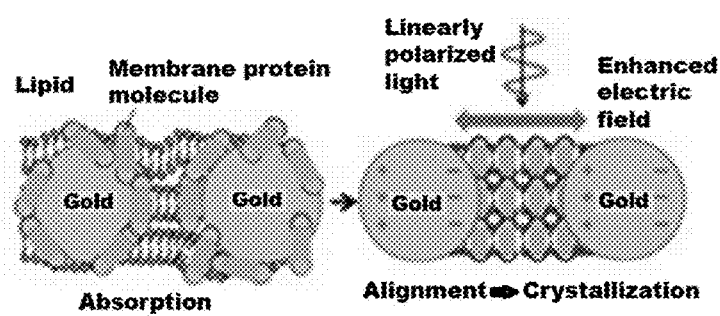
FIG. 11          FIG. 11(a)          FIG. 11(b)

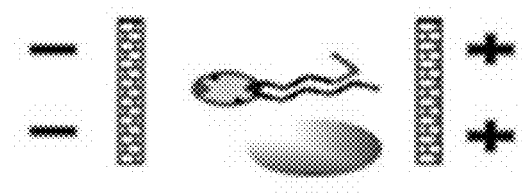 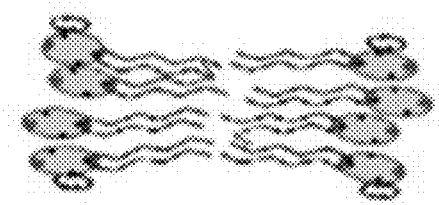
FIG. 14(a)
Prior Art
FIG. 14(b)
Prior Art

_BIOPOLYMER CONCENTRATION METHOD, CRYSTALLIZATION METHOD, AND NANOSTRUCTURED SUBSTRATE_

RELATED APPLICATIONS

The present application is National Phase of International Application No. PCT/JP2020/014992 filed Apr. 1, 2020, and claims priority from Japanese Application No. 2019-085309, filed Apr. 26, 2019, the disclosure of which is hereby incorporated by reference herein in its entirety.

TECHNICAL FIELD

The present invention relates to a biopolymer concentration method, a biopolymer crystallization method, and a nanostructured substrate for biopolymer concentration or crystallization, and particularly relates to a protein concentration and crystallization method and the like.

BACKGROUND ART

Biopolymers include cells, proteins, polysaccharides, ligands, cells, antibodies, antigens, organelles, lipids, blastomeres, aggregates of cells, microorganisms, peptides, deoxyribonucleic acid (DNA), ribonucleic acid (RNA), and fragments thereof. The concentration and crystallization of such biopolymers are important for a vast number of biomedical applications, including diagnosis, treatment, cell biology, and proteomics. For example, crystallization of proteins, particularly crystallization of membrane proteins, is expected to have a wide range of applications, such as structural analysis using X-rays, genome analysis, biosensors, and pharmaceuticals.

The particle size of biopolymers is generally several nanometers to 10 nanometers, and their coupling force is said to be several picoNewtons to several hundred picoNewtons. Since the bonding strength of biopolymers is thus very weak, various methods have been proposed for concentrating or crystallizing biopolymers, and various nanostructured substrates comprising metal fine particles have been proposed. Typical crystal growth methods are a sitting-drop method, a hanging-drop method, a bulk-batch method, a micro-batch method, and the like.

X-ray crystallography is one of the most powerful methods for analyzing biopolymer structures, and good quality crystals are necessary to obtain higher-order structures. However, crystallization is difficult for many biopolymers. In particular, crystallization is difficult for proteins, because protein molecules are anisotropic and their solubility varies depending on the temperature of the solution, the type and pH of buffer solution, the type of crystallizer, etc.

Proteins are classified as water-soluble proteins and membrane proteins. Water-soluble proteins are those that flow in the cytoplasm, and membrane proteins are those that are buried in the biomembrane, partly in contact with the biomembrane, or embedded in the biomembrane. It is known that crystallization is particularly difficult for membrane proteins because they are present in the form buried in the cell membrane.

There have been many cases of successful crystallization of membrane proteins by various methods, and these successful cases can be applied to the crystallization of biopolymers. In the early days, there were crystallization methods in which membrane proteins were solubilized by surfactants, and the solubilized membrane proteins were aggregated by salting out.

For example, claim 1 of JP2007-230841A discloses "a protein crystal formation method for forming a protein crystal from liquid drops of a protein solution, the method comprising step (A) of forming a crystal nucleus by accelerating the vapor diffusion speed of the liquid drops of the protein solution." It is described that any of the ways of placing, i.e., a hanging drop method (a), a sitting drop method (b), and a sandwich drop method (c), can be used (paragraph 104 of this document). This is intended to use a solvent adsorbent or the like to thereby evaporate water from the liquid drops, and as a result to continuously increase the concentration of the protein.

However, in this method, as shown in FIG. 12, the salt component is likely to precipitate between the single-molecules of the protein, and it is difficult to crystallize pure proteins.

Further, claim 1 of JP2014-172833A discloses "a membrane protein crystallization method comprising a preparation step of preparing a composition comprising a membrane protein, a lipid, a surfactant having a hydrophilic part and a hydrophobic part with a photoisomerizable group, and water; and a precipitation step of precipitating membrane protein crystals in the composition." Since the membrane protein is buried in the cell membrane, this method is intended to facilitate the crystallization of the membrane protein using a surfactant.

However, in this method, as shown in FIG. 13, the surfactant component is likely to enter between the single-molecules of the protein, and it is difficult to crystallize pure proteins.

In addition, several methods have been proposed for applying electromagnetic waves, for example, using surface plasmon resonance. Here, surface plasmon resonance is a phenomenon in which when light is irradiated on metal nanoparticles, such as gold and silver, which are sufficiently smaller than the wavelength of light, the electric field of the light causes collective vibration of free electrons present on the surface of the metal nanoparticles, resulting in electrical polarization. FIG. 2 of Journal of the American Chemical Society published on Jul. 21, 2010 (Non-Patent Document 1, described later) shows that when three gold nanoparticles were arranged in an L-shape, a new localized surface plasmon resonance peak was observed on the long wavelength side due to the localized surface plasmon resonance of one gold nanoparticle. Further, FIG. 2 of Journal of Oleo Science published in 2014 (Non-Patent Document 2, described later) explains that when the absorption spectrum of gold nanoparticle colloids after aggregation is observed, the transverse plasmon resonance of a primary chain assembly is observed on the short wavelength side, while the longitudinal plasmon resonance appears on the long wavelength side.

As a substrate using surface plasmon resonance, for example, claim 5 of JP2013-177665A (Patent Document 1, described later) discloses "a metal particle assembly membrane-laminated substrate comprising a substrate and a particle assembly laminated on the substrate, the particle assembly being formed by at least 30 metal particles two-dimensionally disposed apart from one another, wherein the average particle size of the metal particles is in the range of 200 to 1600 nm, the average height of the metal particles is in the range of 55 to 500 nm, the aspect ratio defined as the ratio of the average particle size to the average height is in the range of 1 to 8, and the metal particles are disposed in a manner such that the average distance between adjacent metal particles is in the range of 1 to 150 nm."

Further, the claims of JP5224306B (Patent Document 2) disclose "a biopolymer crystallization substrate, which has a noble metal vapor-deposited film having absorption in a wavelength range of 500 to 1,000 nm on the entire or a part of one surface of the substrate, wherein the absorbance at a wavelength of 600 nm of the noble metal vapor-deposited film is 0.08 to 0.5, the average thickness of the noble metal vapor-deposited film is 0.1 to 60 nm, and the noble metal vapor-deposited film is a continuous film and partly has a depression surrounded by the continuous film and formed by vapor deposition."

Further, there are methods for crystallizing proteins by applying an electric field, which is one of electromagnetic waves. For example, claim 1 of JP2008-137961A (Patent Document 3, described later) discloses "a protein crystallization method comprising adding a reagent necessary for protein crystallization to a protein solution to form a sample solution, and placing the sample solution in a predetermined environment to crystallize the protein in the sample solution, wherein the protein is crystallized while applying, to the sample solution, a voltage that increases the resolution of X-ray diffraction of the precipitated crystals."

When an electric field is applied, polarizing action (electric field polarization) occurs, and the single-molecule of the protein is altered, as shown in FIG. 1 (b). This facilitates the joining of the protein single-molecules to each other, and promotes the clustering of the protein group in which the protein single-molecules aggregate.

However, electromagnetic waves have the property of weakening or strengthening, and also have the property of being easily concentrated in sharp parts. Further, it is known that a local high-temperature region called a hot spot (hot space) is generated when two or three metal nanoparticles come close to each other under an applied electric field.

Therefore, when a complicated nanostructured substrate is placed in a uniform electric field, a local high-temperature region may be generated due to the irregular electromagnetic field. When protein single-molecules enter this high-temperature region, they undergo thermal alteration, as shown in FIG. 14 (a). On the other hand, as is well known, elongated protein single-molecule is easily altered by short wavelength light. This is because although natural biopolymers are stable, solubilized protein single-molecule is prone to photobleaching. When such altered protein single-molecules are mixed in an assembled protein group, the protein group is not clustered, as shown in FIG. 14 (b).

PRIOR ART DOCUMENTS

Non-Patent Documents

[Non-Patent Document 1] "Structure-Activity Relationships in Gold Nanoparticle Dimers and Trimers for Surface-Enhanced Raman Spectroscopy," Journal of the American Chemical Society, published on Jul. 21, 2010, Vol. 132, No. 31, pp. 10903-10910

[Non-Patent Document 2] Takao Fukuoka, Yasuo Mori, "Ultra-sensitive analysis of gold nanoparticle self-assemblies by surface-enhanced Raman scattering," Journal of Oleo Science, published in 2014, Vol. 14, No. 1, pp. 5-10

PATENT DOCUMENTS

[Patent Document 1] JP2013-177665A
[Patent Document 2] JP5224306B
[Patent Document 3] JP2008-137961A

SUMMARY OF THE INVENTION

Problem to be Solved by the Invention

As descried above, there has been no technology until now for controlling the polarizing action (electric field polarization) of electromagnetic waves. Therefore, during bonding of single-molecules of biopolymers, the single-molecules themselves were altered by external electromagnetic waves or the like, assemblies of the single-molecules were altered, or the biopolymers could not be concentrated or crystallized. That is, there were various problems, such as the generation of local high-temperature regions due to electric field polarization.

The present invention has been made in order to solve the above problems. The present invention succeeded in uniformly distributing electromagnetic waves on the light-receiving surface side by taking advantage of their property of being easily concentrated in sharp parts. On the other hand, the present invention succeeded in forming a more moderate electric field region by making the front area ($S_A$) on the emission surface side larger than the back area ($S_B$) on the light-receiving surface side ($S_A/S_B>1$). An object of the present invention is to provide a method for concentrating or crystallizing biopolymers under mild conditions. Another object of the present invention is to provide a nanostructured substrate for biopolymer concentration or crystallization that facilitates the concentration or crystallization of biopolymers.

Means for Solving the Problem

The present invention has the following configurations.

(1) In a biopolymer concentration method for concentrating a biopolymer by impregnating a nanostructured substrate with a biopolymer-containing solution while applying electromagnetic waves, the nanostructured substrate comprises a base material, a base group fixed to the base material, and a metal layer group deposited on the base group, the base group is fixed separately to the base material, and a ratio ($S_A/S_B$) of a geometric front area ($S_A$) in terms of hemisphere on a total emission surface side of the metal layer group and a geometric back area ($S_B$) on a total light-receiving surface side exceeds 1.

(2) In a biopolymer crystallization method for crystallizing a biopolymer by impregnating a nanostructured substrate with a biopolymer-containing solution while applying electromagnetic waves, the nanostructured substrate comprises a base material, a base group fixed to the base material, and a metal layer group deposited on the base group, the base group is fixed separately to the base material, and a ratio ($S_A/S_B$) of a geometric front area ($S_A$) in terms of hemisphere on a total emission surface side of the metal layer group and a geometric back area ($S_B$) on a total light-receiving surface side exceeds 1.

(3) In a nanostructured substrate for biopolymer concentration or crystallization to be irradiated with electromagnetic waves, the nanostructured substrate comprises a base material, a base group fixed to the base material, and a metal layer group deposited on the base group, the base group is fixed separately to the base material, and a ratio ($S_A/S_B$) of a geometric front area ($S_A$) in terms of hemisphere on a total emission surface side of the metal layer group and a geometric back area ($S_B$) on a total light-receiving surface side exceeds 1.

Further, the embodiment items of the present invention are as follows.

(4) In the method according to (1) or (2), the metal layer has a peak-valley structure.

(5) In the method according to (1) or (2), the base group is a metal fine particle group.

(6) In the method according to (1) or (2), the metal layer group is composed of a reductively deposited metal or alloy.

(7) In the method according to (1) or (2), the metal layer group, or the metal layer group and the base group show plasmon characteristics.

(8) In the method according to (1) or (2), the biopolymer is a membrane protein.

(9) In the nanostructured substrate for biopolymer concentration or crystallization according to (3), the metal layer has a peak-valley structure.

(10) In the nanostructured substrate for biopolymer concentration or crystallization according to (3), the base group is a metal fine particle group.

(11) In the nanostructured substrate for biopolymer concentration or crystallization according to (3), the metal layer group, or the metal layer group and the base group show plasmon characteristics.

(12) In the nanostructured substrate for biopolymer concentration or crystallization according to (3), the base material is a resin film with an absorbance of 0.05 or more.

(Principle)

The principle of the present invention will be described below with reference to drawings. The principle of protein crystallization (FIG. 1) in the present invention is basically represented by steps FIG. 1(*a*) to FIG. 1(*f*).

Step (a)

The figure shown in FIG. 1(*a*) schematically illustrates a free protein as a single unit molecule in a supersaturated solution. There is electric field polarization between adjacent deposited layers, in which the protein single-molecule is continuously altered more strongly as the adjacent distance becomes closer. Therefore, the protein molecule adsorbed on the surface of one deposited layer moves toward the valley with a narrower adjacent distance.

Step (b)

The figure shown in FIG. 1(*b*) illustrates the state of the protein molecule located in a region with the strongest electric field polarization. The protein molecule sandwiched between the adjacent deposited layers receives strong electric field polarization, and is thus altered upon strong polarizing action in the horizontal direction.

On the other hand, the side chain of the protein molecule does not receive electric field polarization because of its different polarity. That is, even if the protein molecule in the longitudinal direction receives strong electric field polarization, the side chain of the protein molecule remains activated. This allows joining to the next protein molecule at the side chain.

Step (c)

The figure shown in FIG. 1(*c*) schematically illustrates the state of protein molecules linked in the lowest region toward the back of the paper. The cluster of the linked protein molecules acts as a single molecular unit as a whole. As the electric field polarization weakens toward the back of the paper, a cluster of an appropriate number of protein molecules is cut off from the lowest region due to the Brownian motion.

Steps (d) and (e)

The figure shown in FIG. 1(*d*) illustrates the case in which a new protein molecule falls immediately after the cluster of an appropriate number of protein molecules is cut from the lowest region. The leg of the new protein molecule and the leg of the cut protein molecule are paired by the interaction (FIG. 1(*e*)). New protein molecules constitute a cluster of an appropriate number of subsequent protein molecules as in step (c) above, and eventually the cluster of the previous protein molecules and the cluster of the subsequent protein molecules are paired. If the leg of the cluster of the new protein molecules and the leg of the cluster of the cut protein molecules are not paired in step (e), the clusters of the previous and subsequent protein molecules are considered to be paired in step (f).

Step (f)

The figure shown in FIG. 1(*f*) schematically illustrates the autonomous rearrangement of cluster pairs of protein molecules and free protein single-molecules to form a large number of protein fragments in a reservoir surrounded by peaks in the deposited layer. The cluster pair of protein molecules receives electric field polarization and is thus easily altered, and can be autonomously rearranged to the optimal positions of the protein fragments. In addition, since the rearranged protein fragments are active, there is an effect that they can be concentrated to form more active sites.

In the present invention, the arrangement, number, and surface form of the peaks constituting the deposited layer on the base material can be appropriately selected. For this reason, in the case of membrane proteins that are difficult to crystallize or biopolymers that are easily altered, the volume of the reservoir of the peak-valley structure in step (f) can be made larger or smaller, and the number of reservoirs can be increased or decreased, whereby the crystallization thereof can be appropriately promoted.

The terms of the present invention will be explained below.

(Biopolymer-Containing Solution)

In the present invention, a biopolymer includes a biopolymer single-molecule. Further, a biopolymer-containing solution includes those in which biopolymers are isolated as they are, and those in which biopolymers are ionically dissolved. That is, in the present invention, a solution containing a biopolymer means that the biopolymer may be present as an assembly in the solution, or solubilized as single-molecule. A supersaturated solution is preferred. The (weight average) molecular weight of the biopolymer is preferably 1,000 or more, and more preferably 1,000 or more and 1,000,000 or less.

Specific examples of biopolymers include polypeptides, such as those obtained by expression in *Escherichia coli*, yeast, and animal cells, followed by isolation by a conventional method; proteins; synthetic products, such as synthetic polypeptides and synthetic proteins; and nucleic acids (e.g., DNA); as well as derivatives thereof, such as sugar proteins and DNA conjugates. Of these, preferred biopolymers are polypeptides, proteins, and derivatives thereof; and more preferred biopolymers are proteins and derivatives thereof; and particularly preferred biopolymers are membrane proteins. Further, proteins include enzymes.

For example, the solubility of biopolymers varies depending on the temperature of the solution, the type and pH of buffer solution, crystallizers, surfactants, and the like. The pH is preferably 4 to 8. This is because a biopolymer single-molecule is easily affected by electromagnetic waves. Further, among biopolymers, proteins may be proteins flowing in the cytoplasm, proteins buried in the biomembrane, or proteins partially in contact with or embedded in the biomembrane. For proteins, it is preferable to use a supersaturated solution in the metastable region.

It is preferable that the biopolymer that can be used in the present invention has high purity and homogeneity, because crystals can be produced more easily. Therefore, the biopolymer crystal concentration method of the present invention preferably comprises a step of purifying the biopolymer before the production of crystals. The purification of the biopolymer before crystallization can be performed by a known method, and is preferably performed, for example, by affinity chromatography, conventional chromatography, rpHPLC, FPLC, or the like.

In the case of producing crystals of nucleic acids, it is preferable to isolate them by a known isolation method, and increase their purity by purification, followed by crystallization. Further, in the case of proteins, it is preferable to increase their purity by a known method, and confirm the purity by isoelectric point electrophoresis, light scattering, or the like, followed by crystallization. In addition to the biopolymer, solvent, and crystallizer, known additives may be added, if necessary, to the biopolymer solution. Such additives may be added once or several times.

The biopolymer concentration and crystallization method of the present invention comprises a contact step of bringing the nanostructured substrate of the present invention into contact with the biopolymer solution by immersion. Here, the biopolymer solution may be a liquid containing a biopolymer and a solvent that dissolves the biopolymer, as described above. The biopolymer solution is preferably a solution in which the biopolymer is completely dissolved. The solvent used in the biopolymer solution can be independently selected depending on the biopolymer used. Examples thereof include water, organic solvents, mixture of water and water-miscible organic solvents (aqueous organic solvents), and the like. Water is preferred because the van der Waals force acts on biopolymers.

The concentration of the biopolymer in the biopolymer solution is not particularly limited. For example, a solution with a concentration of 1 to 100% of the saturated concentration or an oversaturated solution can be used. The concentration of the biopolymer is preferably 80% or more, and more preferably 90% or more, of the saturated concentration, and particularly preferably a saturated or supersaturated concentration. Further, in order to maintain the solution concentration, for example, the biopolymer, which is a solute, may be replenished, the temperature may be lowered, or a precipitant may be further added.

Further, the biopolymer solution of the present invention may contain a crystallizer. Here, the crystallizer refers to a compound that works to reduce the solubility of polymers, preferably biopolymers. Examples thereof include compounds such as precipitants, pH buffers, and other additives used for the crystallization of polymers. Examples of crystallizers include salts, organic solvents, water-soluble polymers, and the like, and known crystallizers can be used. Moreover, the type of crystallizer used may be appropriately set depending on the type of biopolymer used.

Examples of salts that can be used include sulfates, nitrates, phosphates, organic acid salts, halides of alkali metals or alkaline earth metals, and the like. Specific examples include ammonium sulfate, sodium chloride, and sodium citrate. Examples of organic solvents include water-soluble organic solvents. Specifically, for example, 2-methyl-2,4-pentanediol (MPD), ethanol, or propanol dioxane can be used. Examples of water-soluble polymers include polyethylene glycol, polypropylene glycol, and the like. The amount of the crystallizer added is not particularly limited, and may be appropriately set depending on the type of biopolymer used and the type of crystallizer used.

(Peak-Valley Structure)

In the present invention, when the nanostructured substrate is viewed from the total emission surface side of the metal layer group, the metal layer group preferably has a peak-valley structure. It is more preferable that the base group is a metal fine particle group. It is even more preferable that the composite particle group of the metal layer group or the metal layer group and the base group show plasmon characteristics. Moreover, the peak-valley structure is preferably a smooth continuous film on the total emission surface side of the metal layer group. In the case of a nanostructured substrate having no deposited metal layer group, and consisting of a base group in which adjacent metal fine particles are fixed separately to the base material, the ratio ($S_A/S_B$) of the geometric front area ($S_A$) in terms of hemisphere on the total emission surface side and the geometric back area ($S_B$) on the total light-receiving surface side is 1.

The peak-valley structure of the metal layer group specifically refers to a state in which when the nanostructured substrate is observed from the surface under a microscope, black groove patterns are observed on the boundary between the metal layers. Since the cohesion force of the deposited particles that form the metal layers is strong, when the deposition time is slightly increased, the deposited particles bury the valley structure and are deposited horizontally. Such horizontally deposited thin layers have been called uniform thin layers or ultrathin layers in the plating industry. In such a case, the ratio ($S_A/S_B$) of the geometric front area ($S_A$) in terms of hemisphere on the total emission surface side of the metal layer group and the geometric back area ($S_B$) on the total light-receiving surface side is less than 1. In the present invention, the structure of the metal layer group whose film thickness is up to 300 nm before reaching to an ultrathin layer is called the peak-valley structure.

When the nanostructured substrate with a peak-valley structure is subjected to low-temperature heat treatment at 200° C. or lower, for example, strain relief heat treatment, so-called metal recovery heat treatment, of the deposited particle group by wet plating can be performed. As a result of the recovery heat treatment, the exposed surface of the deposited particle group is reorganized. When the peak-valley structure of the reorganized deposited particle group is observed, the contours of the peaks and valleys become clear.

(Metal Layer)

In the present invention, the metal layer is a layer of metal deposited from the liquid or gas phase. It is a layer of so-called wet-plated or dry-plated metal. The liquid phase is preferred, and a layer reductively deposited from an aqueous solution, for example, by wet plating is more preferred. Various plating methods, such as replacement plating, chemical plating, electroless plating, and electroplating, can be used for wet plating. More preferred is a metal layer obtained by wet plating, such as replacement plating, chemical plating, or electroless plating, and particularly preferably electroless plating that causes autocatalytic deposition. This is because it is easy to obtain a composite particle group comprising metal layers of unequal height. The active surface of such a composite particle group can be used for adsorption and desorption of biopolymers. In wet plating, it is particularly preferable to perform plating operations using an autocatalytic electroless plating solution or replacement plating solution, both of which have an extremely slow deposition rate.

Further, the metal of the metal layer is preferably gold, silver, platinum, palladium, or an alloy thereof. In particular, gold and silver are preferred. This is because the best peak-valley structure can be confirmed due to their plasmon expression. Alloys can be subjected to eutectoid plating. For example, non-metals, such as carbon black, silicon oxide, or titanium oxide aerosols, may be added to the electroless plating solution.

In the case of a metal layer composed of gold-deposited particles, plasmon absorption is observed at around 530 nm, even though the shape of the peak-valley structure is different. When the base group is a metal fine particle group, the shape is composed of a small hemisphere and a large hemisphere joined together. The wavelength of the plasmon absorption depends on the metal species of the deposited particle group. In addition, the Dharma-like plasmon intensity due to the gold-deposited particle group of the present invention is red-shifted dependently on the increase in plating time, i.e., the total weight of the deposited particle group.

(Fine Particles)

In the nanostructured substrate for concentration or crystallization of the present invention, the reason that the fine particles are fixed separately to the substrate is to distribute the incident electromagnetic waves uniformly in the base group. The material of the fine particles is not particularly limited. Metal, ceramic, glass, plastic, and other various materials can be used. The fine particles can be aligned horizontally at intervals by an inkjet or 3D printer. When a small hemisphere is formed by inkjet or the like, a shape in which a large hemisphere is joined on the small hemisphere is formed. The fine particles can also be formed by dry plating, such as vacuum vapor deposition. Furthermore, a base material that is transparent to visible light can be provided with V-grooves or recesses to align the fine particles.

The fine particles are preferably made of metal or an alloy. This is because the electromagnetic waves can be absorbed into the fine particles, and new electromagnetic waves can be emitted from the surface of the fine particles. For the material of the fine particles, it is preferable to use the same type of metal as for the metal layer. The fine particles are preferably wet-reduced from a solution, particularly an aqueous solution.

The fine particles may have various shapes, such as a sphere, prolate spheroid, cube, truncated tetrahedron, bipyramid, regular octahedron, regular decahedron, and regular icosahedron. The fixed end is preferably buried in a hemispherical shape. When using a suitable dispersant, the fine particles can be self-assembled at predetermined intervals. For example, self-assembly is illustrated in JP2017-524829A. It is described that a reducing agent is added to an aqueous solution in which metal ions are dissolved, so that spherical metal fine particles with a diameter ranging from 5 to 200 nm (oxidation state=0) are reduced. In paragraphs 0077 to 0081 of this patent document, various stabilizers such as surfactants are used to prevent the aggregation of the metal fine particles. By using such a surfactant, fine particles can be dispersed relatively uniformly; thus, some of the detached fine particles can be easily fixed on the base material.

When the ends of the fine particles fixed to the substrate are reduced fine particles, the average particle size of the fine particles is preferably 10 to 200 nm. The average particle size is more preferably 5 to 50 nm. Further, the lower limit is preferably 10 nm or more. This is because the nanoparticle group is less likely not to become the nucleus of the metal layer group when the average particle size is less than 10 nm. The lower limit is particularly preferably 15 nm or more. On the other hand, if the upper limit of the average particle size of the fine particles exceeds 50 nm, the biopolymer may be less likely to be adsorbed. The upper limit is more preferably 40 nm or less. The intervals of the fine particles are preferably 40 nm or less. The intervals of the fine particles are more preferably 30 nm or less. When fine particles of reduced metal are self-assembled, the intervals of the fine particles are generally 10 nm or less.

The exposed surface of the fine particles serves as the deposited nucleus of the deposited particle group. For this reason, the fine particles and the metal layer are preferably made of the same type of metal. It is more preferable that the metal fine particles are fine particles reduced in an aqueous phase. In particular, self-assembled fine particles are desirable.

(Irradiation of Electromagnetic Waves)

In the present invention, the nanostructured substrate is irradiated with electromagnetic waves. This is because electric field polarization occurs from the composite particles due to the incident electromagnetic waves, and this electric field polarization acts on the biopolymer. When the nanostructured substrate of the present invention is used, the biopolymer is less likely to be altered or deteriorated since polarizing action by the electromagnetic waves is relieved. The output power of the electromagnetic wave generator can be dimmed. Further, the ratio ($S_A/S_B$) of the front area ($S_A$) and the back area ($S_B$) can be set to 1.05 or more.

Here, the geometric front area ($S_A$) in terms of hemisphere refers to the total front area ($S_A$) of a hemisphere group when the metal layer is dissolved in a solution from the nanostructured substrate, and hemispheres with the same geometric shape are formed based on the total weight of the metal layer determined from the solution. On the other hand, the geometric back area ($S_B$) in terms of hemisphere is, when the base group is a metal fine particle group, obtained by multiplying the geometric back area ($S_B$) in terms of hemisphere determined from the average particle size of the metal fine particle group dispersed in the solution by the number of pieces on the base material, and further combining this value and the area of the non-fixed part of the base material. It does not mean the actual front area.

The wavelength of the light irradiated in the electromagnetic wave irradiation step is not particularly limited, but is preferably longer than 400 nm, more preferably 450 to 2,000 nm, even more preferably 600 to 1,500 nm, and particularly preferably 600 to 1,200 nm. Further, the light irradiated in the electromagnetic wave irradiation step may be monochromatic light or continuous light. Circularly polarized or linearly polarized waves are preferred. The particle size of the fine particles fixed to the base material can be relatively increased as the wavelength becomes longer.

In the present invention, in the case of visible light, the wavelength is preferably 400 nm to 780 nm. When using near-infrared light, the wavelength is preferably longer than 780 nm and 2,500 nm or less, and more preferably longer than 780 nm and 2,000 nm or less. Although the intensity of the light to be irradiated can be appropriately selected, light with an intensity in the range of several μW to several 100 W can be generally used.

The electromagnetic waves to be irradiated may be steady waves or pulse waves. The irradiation intensity, energy per pulse, pulse interval, and the like can be changed, if necessary. The electromagnetic wave irradiation is preferably performed by applying steady light continuously, but may be performed intermittently or interrupted. The irradiation time is not particularly limited, and may be continuous or intermittent until crystals are formed.

Further, the electromagnetic wave irradiation means can be composed of, for example, a light source and an optical system for guiding light to the solution. As the optical components, such as lenses and mirrors, used in the optical path guiding light from the light source to the irradiated sample, it is preferable to use those that transmit or reflect light efficiently. Steady light sources and laser light sources mentioned above can be used as the light source. In addition, optical members, such as reflectors, light-collecting lenses, optical filters, infrared-blocking filters, optical fibers, light guide plates, and nonlinear optical elements, can be used in the above optical system, as appropriate.

For example, the biopolymer supersaturated solution can be irradiated with nanosecond near-infrared pulsed laser. Further, the single-molecules of the biopolymer can be captured by the light pressure of focused near-infrared laser. Moreover, when electromagnetic waves are applied, a photo-functional surfactant with a photoisomerizable azobenzene skeleton can also be added to a lipid cubic phase.

(Base Material)

In the nanostructured substrate of the present invention, the base material is preferably a resin film or glass with an absorbance of 0.01 to 1.0 at a wavelength of 600 nm. The base material is more preferably a resin film with an absorbance of 0.05 or more. This is because resin films are more convenient than glass. Examples include polyimide resin, polyamide acid resin, fluorene resin, polysiloxane resin, polyethylene terephthalate resin, polyphenylene ether resin, epoxy resin, fluororesin, vinyl resin, phenol resin, ion-exchange resin, and the like. This resin material may be composed of a single resin or a mixture of a plurality of resins.

(Crystallization Container)

The crystallization container of the present invention is a crystallization container comprising the nanostructured substrate of the present invention. Further, in the crystallization container of the present invention, the container itself and the nanostructured substrate of the present invention may or may not be physically or chemically bonded. Specifically, for example, a lid of the nanostructured substrate of the present invention may be attached to the crystallization container of the present invention, or the nanostructured substrate of the present invention may be simply placed in the container. Further, the crystallization container of the present invention may have one nanostructured substrate of the present invention, or may have two or more of them. When the crystallization container of the present invention has two or more nanostructured substrates of the present invention, particularly have many of them, samples can be treated in parallel at the same time.

The shape of the crystallization container of the present invention is not particularly limited as long as it can bring the peak-valley structure in the nanostructured substrate of the present invention into contact with a solution containing a substance to be crystallized, and a desired shape can be used. The crystallization container of the present invention is preferably a sealable container in order to prevent the evaporation of the solution containing a substance to be crystallized during crystallization. It is also preferable that the crystallization container of the present invention is at least partially transparent. The size of the crystallization container of the present invention is not particularly limited, and may be appropriately selected, as needed.

(Storage Step)

The biopolymer concentration method of the present invention may further comprise a storage step of storing the solution of the concentrated biopolymer group in a cold and dark place. The storage step may be performed at the same time as the electromagnetic wave irradiation step. For example, while applying electromagnetic waves, the solution of the biopolymer group may be allowed to stand still to produce crystals.

The storage time can be appropriately selected under conditions in which the biopolymer group can be sufficiently grown. For example, the storage time may be appropriately determined in consideration of the biopolymer group, the crystallizer, the type of solvent used, the formation of crystals, the size of crystals formed, and the like. Moreover, the temperature during storage is not particularly limited as long as it is not a temperature at which the crystallization of the biopolymer group is prevented. In addition, the temperature during storage may be kept constant or changed; however, the temperature change is preferably within 1° C.

Further, the solution of the biopolymer group in the storage step may be stored by placing it in a sealed container or a non-sealed container. In the inside and outside of the container, the amount of the solvent in the atmosphere and, for example, the humidity, can be appropriately set, as needed. Moreover, the atmosphere inside and outside the container can be appropriately selected according to the type of biopolymer group used, and may be, for example, an air, nitrogen, or argon atmosphere.

In addition, in the storage step, the solution may be stored stationary or under stirring, and vibration may be applied continuously, intermittently, or temporarily. The solution can be stored while stirring. Further, large-sized crystals may be obtained by applying micro-vibration in the storage step. The frequency of stirring in the storage step is preferably 10 rpm or more and 300 rpm or less, more preferably 20 rpm or more and 100 rpm or less, and even more preferably 30 rpm or more and 60 rpm or less.

As the vibration means, known vibration, stirring, or ultrasonic wave generating means can be used. The oscillator used in the vibration means is not particularly limited as long as it can apply vibration, and examples thereof include those with various configurations, such as piezoelectric oscillators, suction force, and electromagnetic force. Examples of the method for applying micro-vibration to the biopolymer solution include a method in which a container containing the solution in which the biopolymer is dissolved is brought into contact with a vibration means that is vibrating; and a method in which a container containing the solution in which the biopolymer is dissolved is fixed to a plate, and the whole plate is vibrated.

The storage means is not particularly limited as long as, for example, it can store the noble metal film and the biopolymer solution in contact with each other. However, the storage means is preferably a means that allows the noble metal film and the biopolymer solution in contact with each other to stand still, and more preferably a means that allows the noble metal film and the biopolymer solution in contact with each other to stand still in a sealed space.

Examples of the temperature-adjusting means include known heating means, cooling means, and a combination thereof. Further, the temperature detection can be performed by detecting the internal temperature of the biopolymer solution, the mixed solution, or the like, or by detecting the ambient outside temperature. The temperature-adjusting means may also comprise a programmed circuit to perform the required temperature adjustment.

(Others)

Further, the mode of crystallization in the biopolymer concentration method of the present invention is not particularly limited, and a known method can be used. In particular, when biopolymers are crystallized, for example, a hanging drop vapor diffusion method, a sitting drop vapor diffusion method, a sandwich drop vapor diffusion method, a micro-dialysis method, a free-interface diffusion method, or a storage batch method can be suitably used. For other conditions for promoting the crystallization of biopolymers, reference can be made, for example, to Tsunehiro Takano, New Biochemical Experimental Course 1 "Protein I—Separation, Purification, Nature —," Chapter 14 "Crystallization," edited by The Japanese Biochemical Society; and A. McPherson, "Preparation and Analysis of Protein Crystals" (John Wiley & Son, Inc.).

The device that can be used for the biopolymer concentration method of the present invention is not particularly limited, and known means and devices may be combined. The device that can be used for the biopolymer concentration method of the present invention preferably comprises an electromagnetic wave irradiation means for irradiating the noble metal film with light, and may optionally comprise various means, such as solution preparation means, temperature-adjusting means, humidity-adjusting means, stirring means, vibration means, storage means, crystal formation determination means, and additive-adding means. Further, in the biopolymer concentration method of the present invention, two or more devices having one or more necessary means may be used in combination, or a single device having all the necessary means may be used.

Moreover, the device that can be used in the biopolymer concentration method of the present invention may comprise, if necessary, a device, circuit, or program for detecting and controlling the formation of crystal nuclei in the solution, the pH of the solution, and the like. For the detection and control of crystal conditions, it is preferable to use a single-chip device with multiple cells for detecting crystal conditions. Such a detection chip can be produced by a general production process for semiconductor devices, as described in JP2001-213699A. Further, the device that can be used in the crystallization of the present invention, in particular, the biopolymer concentration method, may comprise a means using laser light with a wavelength that does not contribute to the formation of crystal nuclei or to the crystal growth, but is not absorbed by the biopolymer for detecting the formation state of crystal nuclei, as described in JPH06-116098A.

The biopolymer crystals obtained by the biopolymer concentration method of the present invention can be used not only as samples for X-ray crystallography, but also as preventive or therapeutic dosage forms in pharmaceutical compositions because their storage stability is generally very high. Because the biopolymer has a crystal form, particularly advantageous administration is possible. The biopolymer crystals are suitable, for example, for oral, subcutaneous, intracutaneous, intraperitoneal, intravenous, or intramuscular administration. The biopolymer crystals obtained by the biopolymer concentration method of the present invention can be preferably used as active substances in pharmaceutical compositions comprising a pharmacologically effective amount of the crystallized biopolymer and optionally one or two or more conventional pharmaceutically acceptable carriers.

In addition, the biopolymer crystals obtained by the biopolymer concentration method of the present invention can be used, in principle, as a depot formulation for administering a pharmacologically effective daily dose of 0.001 µg/kg to 100 mg/kg body weight of the biopolymer in a pharmaceutical preparation in the same manner that is known for many biopolymers. Therefore, a wide range of various biopolymers in the form crystallized by the present invention can be used, for example, as therapeutic agent depot formulations, antigen depot formulations, DNA depot formulations, or sugar depot formulations. The crystallization aid contained in the crystals can also be used as an adjuvant (for vaccination).

The device that can be used in the biopolymer concentration method of the present invention may comprise, if necessary, various means, such as solution preparation means, storage means, temperature-adjusting means, humidity-adjusting means, stirring means, vibration means, crystal formation determination means, and additive-adding means. Further, two or more devices having one or more such necessary means may be used in combination, or a single device having all the necessary means may be used.

Effects of the Invention

The biopolymer concentration method of the present invention has the effect that the biopolymer is gently concentrated everywhere in the peak-valley structure, and a concentrated layer of the biopolymer is formed on the nanostructured substrate. It is considered that biopolymer clusters are produced everywhere in the peak-valley structure. Furthermore, the biopolymer crystallization method of the present invention has the effect that such a concentrated layer formed on the horizontal plane on the nanostructured substrate serves as a biopolymer crystal nucleus, and biopolymer group crystals can be gently grown on the nanostructured substrate.

On the other hand, the nanostructured substrate for biopolymer concentration or crystallization of the present invention has the effect that since the incident electromagnetic waves are uniformly distributed, homogeneous electromagnetic waves can be emitted. In addition, since the geometric front area ($S_A$) in terms of hemisphere on the total emission surface side is larger than the geometric back area ($S_B$) on the total light-receiving surface side, there is an effect that the emitted electromagnetic waves are weaker than the incident electromagnetic waves. Furthermore, since biopolymer clusters are produced everywhere in many peak-valley structures, there is an effect that they are not affected by variations in the peak-valley structures. Accordingly, there is an effect that it is possible to select a nanostructured substrate that is optimal for the biopolymer. In addition, there is an effect that it is possible to select a metastable solution suitable for this optimal nanostructured substrate, and to select electromagnetic waves with a wavelength suitable for this optimal nanostructured substrate.

Furthermore, the nanostructured substrate of the present invention has the effect that the size and interval of the fine particles fixed to the substrate can be adjusted according to the type of incident electromagnetic waves. Moreover, there is an effect that the metal species and surface form of the peak-valley structure can be appropriately changed according to the metastable solution of the biopolymer. In addition, when the peak-valley structure is a particle group deposited by wet plating, there is an effect that even nanostructured substrates with a wide area ranging from 1 $\mu m^2$ to 100 $cm^2$ can be easily mass-produced.

BRIEF DESCRIPTION OF DRAWINGS

FIG. 10 is a micrograph of an example.

FIG. 11 is a micrograph of an example, and FIGS. 11(a) and 11(b) are conceptual diagrams of membrane protein.

FIGS. 14(a) and 14(b) are conceptual diagrams for explaining a conventional example.

Next, the examples of the present invention will be described in detail, together with the comparative example and conventional examples, with reference to the drawings. However, the present invention is not limited to these examples. The metal sheet of the present invention can be achieved with various modifications within the scope of the technical idea of the present invention.

COMPARATIVE EXAMPLE

Figure 1:
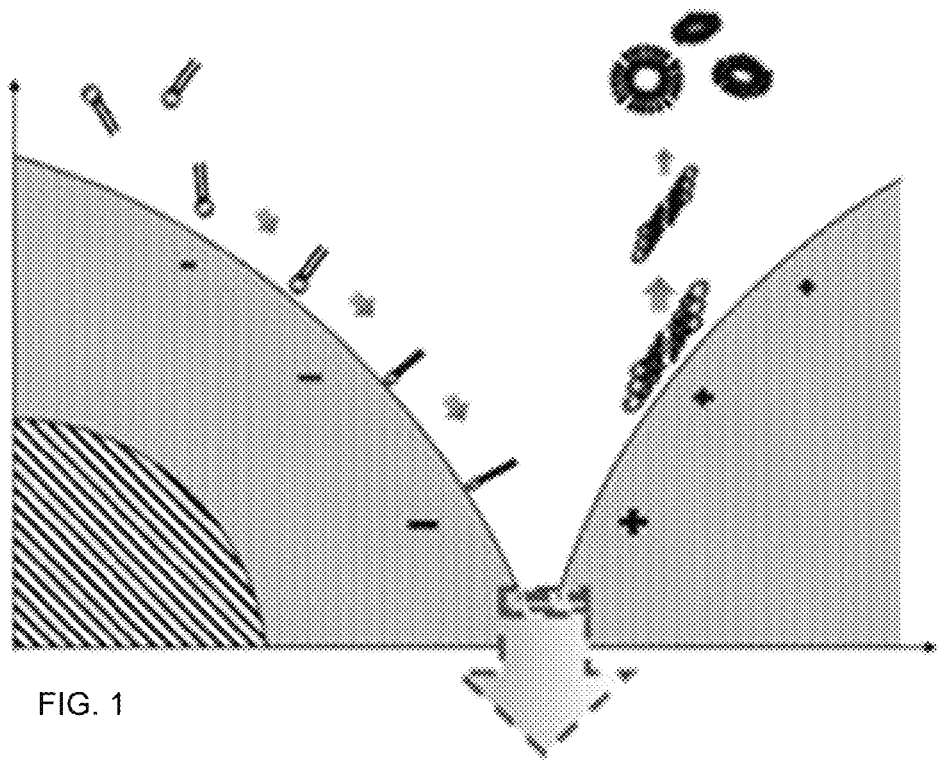
FIG. 1 shows a principle of protein crystallization.
Figure 1A:
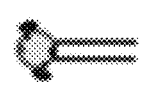
FIGS. 1(a)-1(f) are conceptual diagrams for explaining the principle of the present invention.
Figure 1B:
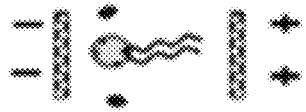
Figure 1C:
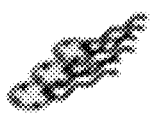
Figure 1D:
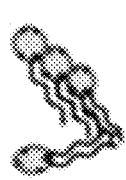
Figure 1E:
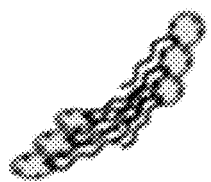
Figure 1F:
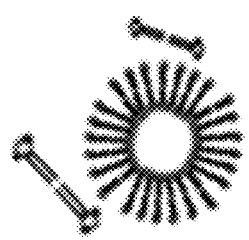
Figure 2:
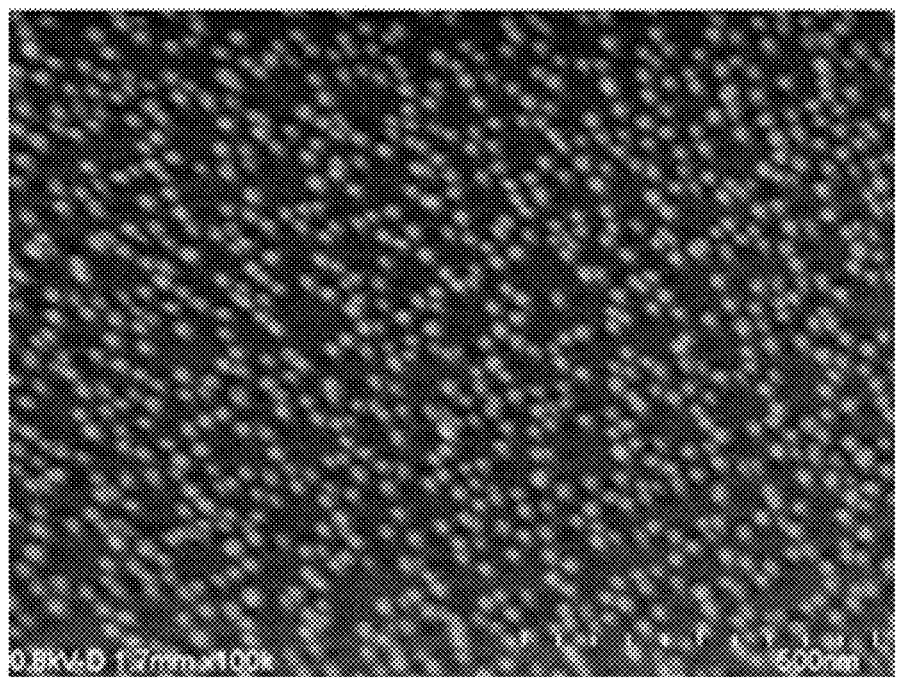
FIG. 2 is a view showing the fine particle group of a comparative example.
Figure 6:
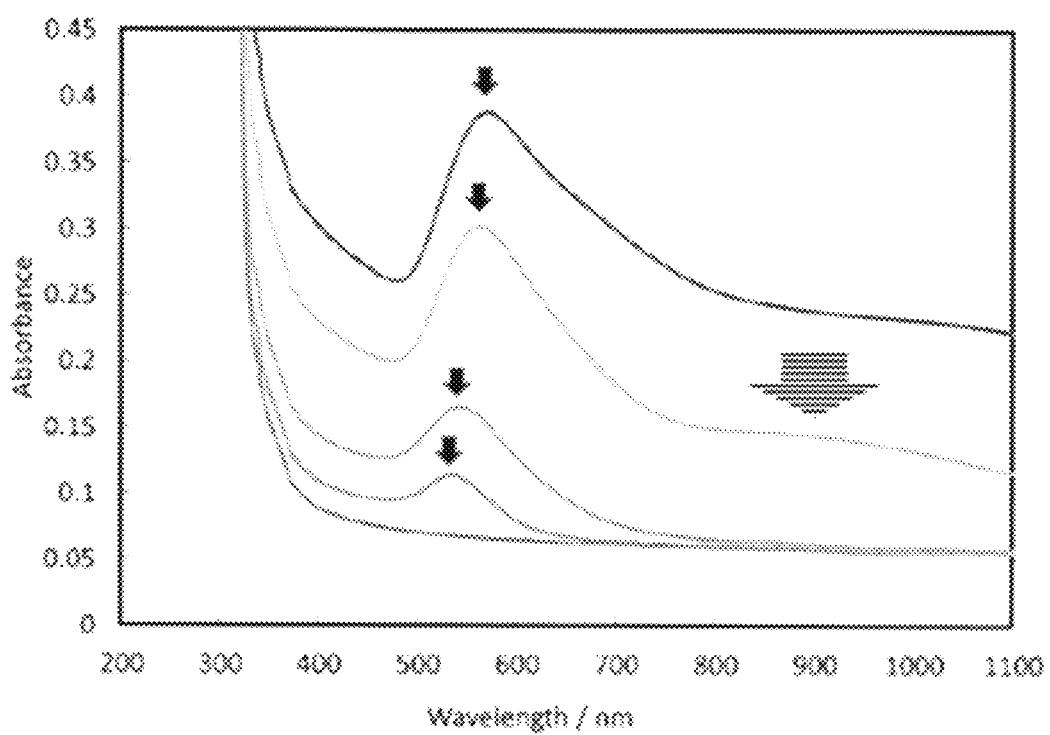
FIG. 6 is a view showing the electric field polarizations of the examples and comparative example.

A reduced gold fine particle group (average particle size: 20 nm) was self-assembled on a transparent, semi-curable polyester resin film (glass transition temperature (measured value): 140° C., the absorption spectrum curve is the lowest curve in FIG. 6), and the reduced gold fine particle group was half-submerged and fixed by predetermined heat treatment. This is shown in FIG. 2. The absorption spectrum curve is the second curve from the bottom in FIG. 6. The ratio ($S_A/S_B$) of the geometric front area ($S_A$) and back area ($S_B$) is 1. A protein crystallization experiment was carried out in the same manner as in Example 1, described later, except for using this nanostructured substrate. No crystals were deposited even after 7 days passed.

Example 1

Figure 4:
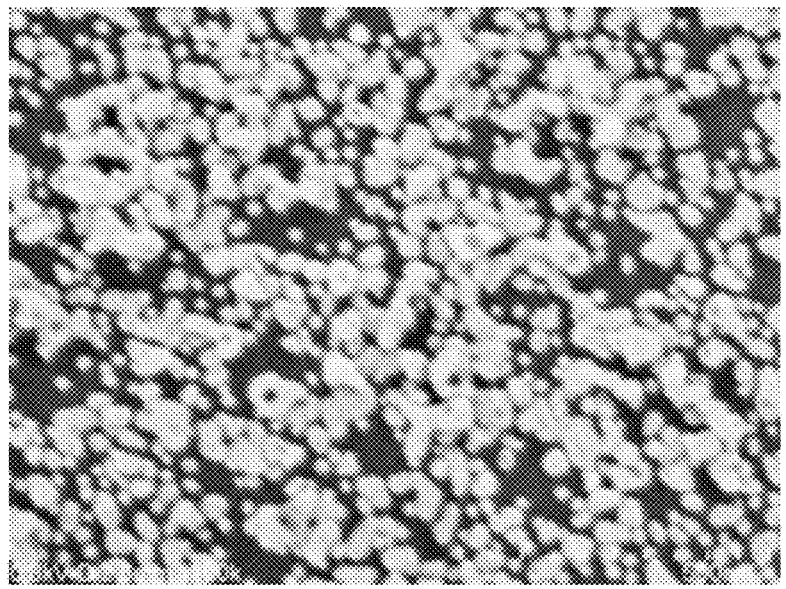
FIG. 4 is a view showing an example.

Next, this transparent base material was immersed in an electroless gold plating solution (an improved bath of Preciousfab ACG3000WX, produced by Electroplating Engineers of Japan Ltd.) at 60° C. for 15 seconds, which was taken as 1 cycle. This step was repeated for 6 cycles to obtain a gold metal layer. Specifically, this is a composite particle group in which gold particles are deposited on the fixed gold fine particles. This is shown in FIG. 4. It is obvious that the geometric front area ($S_A$) in terms of hemisphere on the total emission surface side of the metal layer group shown in FIG. 4 is larger than the geometric back area ($S_B$) on the total light-receiving surface side.

As is clear from FIG. 4, an enormous number of peak-valley structures are observed. L-shaped block structures are formed in various places of the peak area. The L-shaped block still shows a peak-valley structure of multiple composite particles. The absorption spectral distribution of the nanostructured substrate was examined. This absorption spectrum curve is shown as the second curve of the example from the top in FIG. 6. As for this diameter-increasing effect of Example 1, the peak value of plasmon due to the horizontal electric field polarization is red-shifted from around 530 nm to around 580 nm. In other words, this shift indicates that the apparent aspect ratio increases. Further, the plasmon due to the vertical electric field polarization is observed at around 870 nm on the right side of the curve. This plasmon peak curve is similar to the plasmon peak curve of a nanorod.

<Protein Crystallization>

A chicken egg white lysozyme was used as the protein. The protein concentration was 15 mg/mL, and a NaCl 0.5/M solution was prepared as a precipitant. The degree of supersaturation of this solution is 1.25, and it is a metastable solution in which spontaneous crystallization does not occur despite the supersaturation.

Figure 7:
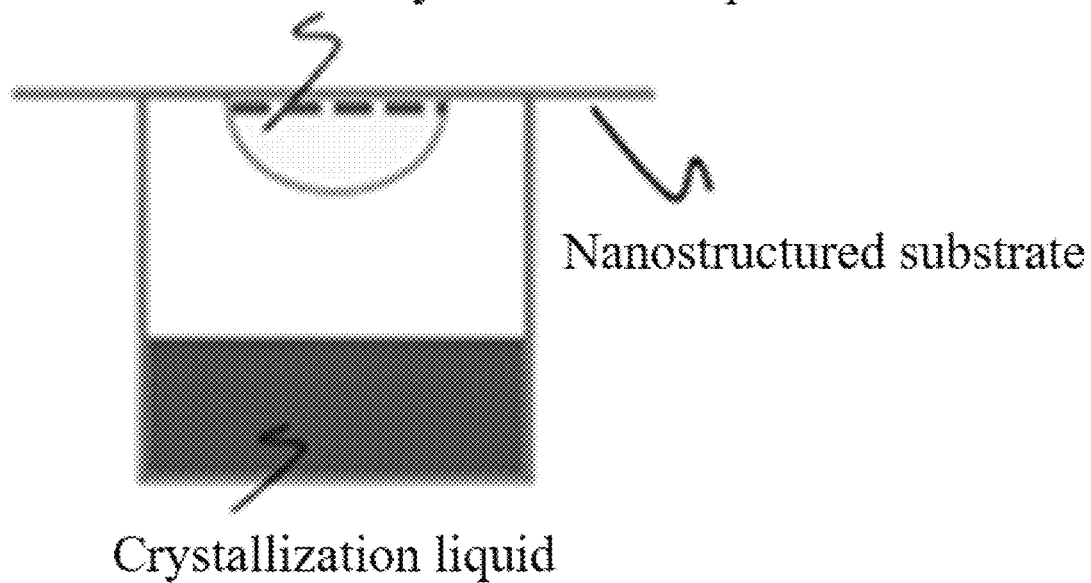
FIG. 7 is a conceptual diagram for explaining the examples.

Crystallization was performed by a hanging drop vapor diffusion method, as shown in FIG. 7. 10 microliters of a protein solution was added dropwise to the peak-valley structures of the nanostructured substrate shown in FIG. 4. The nanostructured substrate was turned over, and the chamber was sealed to prevent the evaporation of the protein solution. The chamber was filled with a reservoir solution containing sodium chloride at the same concentration as that of the dropped protein solution. After 1-hour irradiation with light of a xenon lamp through a cut-off filter for cutting a wavelength of less than 600 nm, the resultant was allowed to stand in a thermostatic incubator at 20° C.

Figure 8:
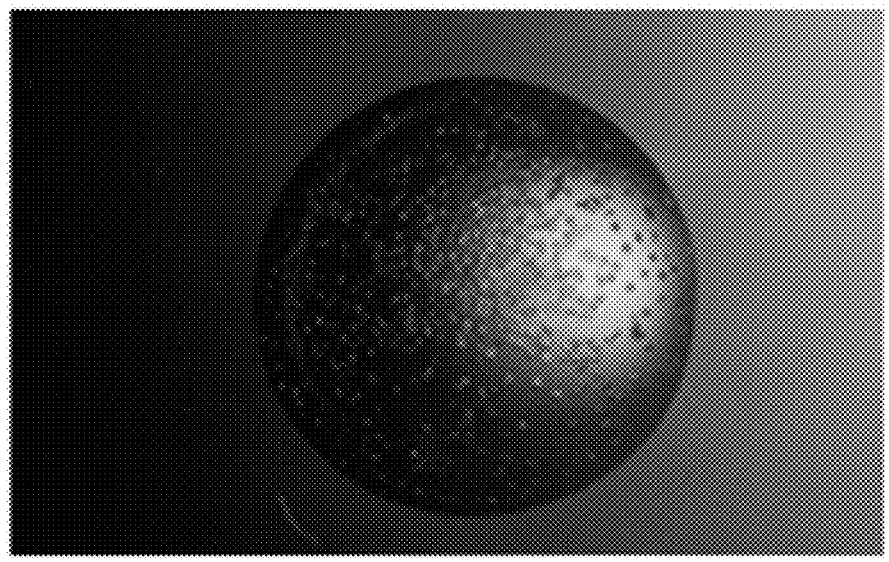
FIG. 8 is a micrograph of the example.

When observed one day after the experiment was started, fine crystals appeared, as shown in FIG. 8. The appearance of fine crystals supports the fact that more crystal nuclei were formed. That is, it is revealed that crystallization was promoted through a series of steps of concentrating the protein single-molecules due to the electric field polarization of the gold metal layer reductively deposited on the gold fine particle group, and forming more crystal nuclei.

Example 2

A protein crystallization experiment was carried out in the same manner as in Example 1, except that the light from the xenon lamp was linearly polarized using a polarizer. In comparison with Example 1, about four times as many crystals appeared. This result reveals that due to the electric field polarization of the nanostructured substrate shown in FIG. 4, the protein adsorbed and aligned on the gold surface was concentrated, and the formation of crystal nuclei proceeded simultaneously over a wide area.

Example 3

Figure 5:
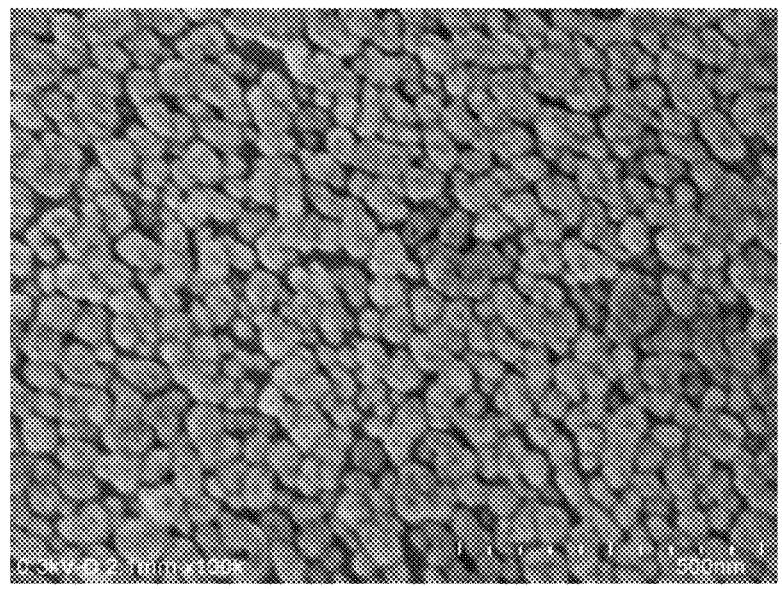
FIG. 5 is a view showing an example.
Figure 9:
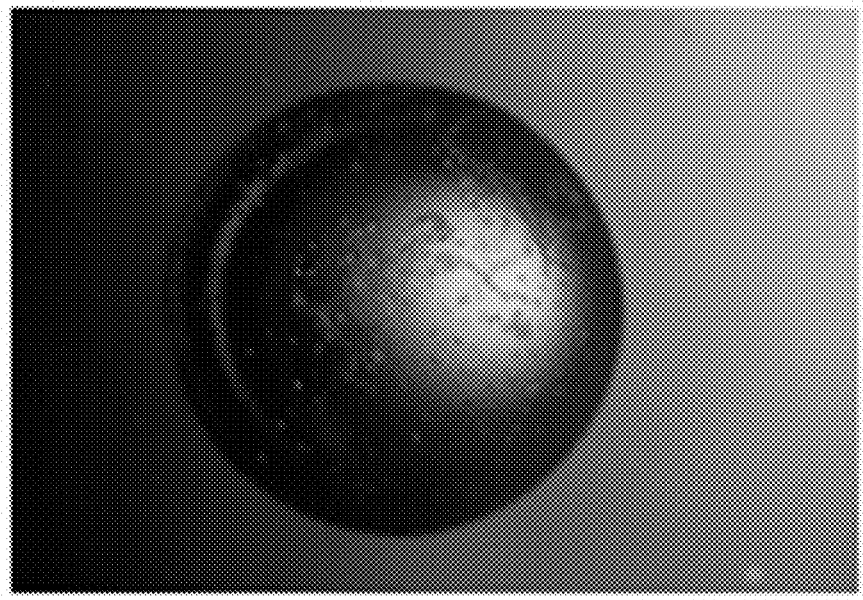
FIG. 9 is a micrograph of the example.
Figure 12:
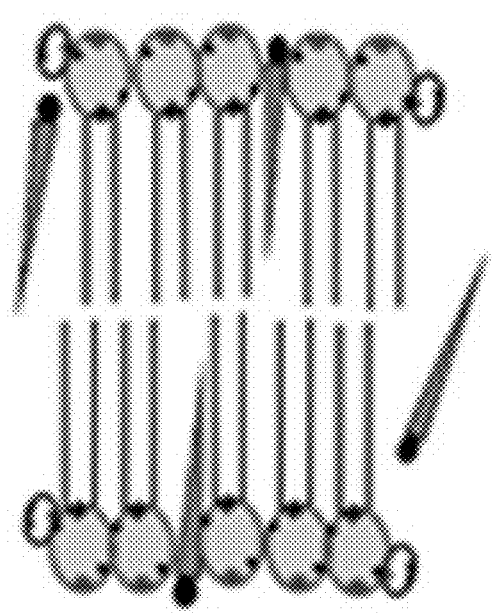
FIG. 12 is a conceptual diagram for explaining a conventional example.
Figure 13:
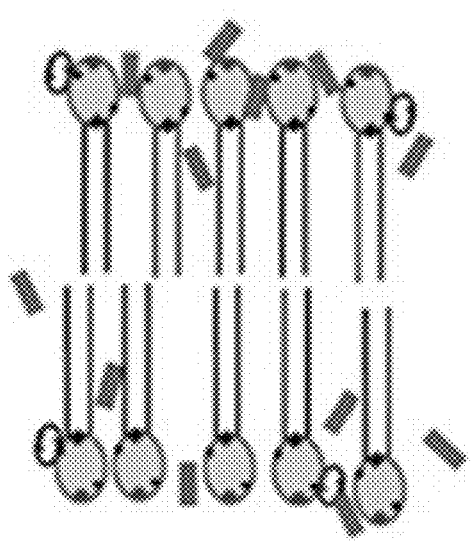
FIG. 13 is a conceptual diagram for explaining a conventional example.

Example 1 was repeated, except that the gold plating step was repeated for 9 cycles to obtain a gold metal layer. This is shown in FIG. 5. The absorption spectrum curve is the uppermost curve in FIG. 6. A crystallization experiment was carried out in the same manner as in Example 1, except for using this nanostructured substrate. It is obvious that the ratio ($S_A/S_B$) of the geometric front area ($S_A$) and back area ($S_B$) exceeds 1. When observed one day after the experiment was started, many fine crystals appeared, as shown in FIG. 9.

Example 4

A silver metal layer was formed in the same manner as in Example 1, except for using electroless silver plating. A 4-well simultaneous crystallization experiment was carried out in the same manner as in Example 1, except for using this nanostructured substrate. When observed one day after the experiment was started, many fine crystals appeared in one out of the four wells.

Example 5

As a membrane protein, the highly halophilic bacterium *Halobacterium salinarum* was cultured to obtain solubilized bacteriorhodopsin that was concentrated to 19 mg/mL. This solution was mixed with monoolein lipid having a water content of 40% w/w to form a cubic phase. As a salt solution, a 3 molar Na/phosphate buffer solution (pH=5.5) was used to adjust the salt concentration to 2.0 M.

A 4-well simultaneous crystallization experiment was carried out in the same manner as in Example 1, except for using this membrane protein solution. When observed after 28 days, crystals appeared in one out of the four wells. This is shown in FIG. 10.

Example 6

A 4-well simultaneous crystallization experiment was carried out in the same manner as in Example 1, except that 7 days later, light from a xenon lamp was applied through a cutoff filter for 1 hour. When observed after 14 days, crystals appeared in two out of the four wells. Further, after 28 days, crystals of the membrane protein appeared in three out of the four wells.

The crystals of the membrane protein after 14 days had the same size as in FIG. 10. The crystal photograph of the membrane protein after 28 days was larger than 50 μm, as shown in FIG. 11 (left micrograph). The micrographs shown in FIGS. 10 and 11 indicate that the crystal size of the membrane protein increases with the number of times of xenon lamp irradiation. That is, FIGS. 10 and 11 show that due to the electric field polarization of the nanostructured substrate shown in FIG. 4, the membrane protein was concentrated (FIG. 11(*a*)), the cluster formation was promoted (FIG. 11(*b*)), and the network of crystal nuclei progressed over a wide area.

Example 7

Figure 3:
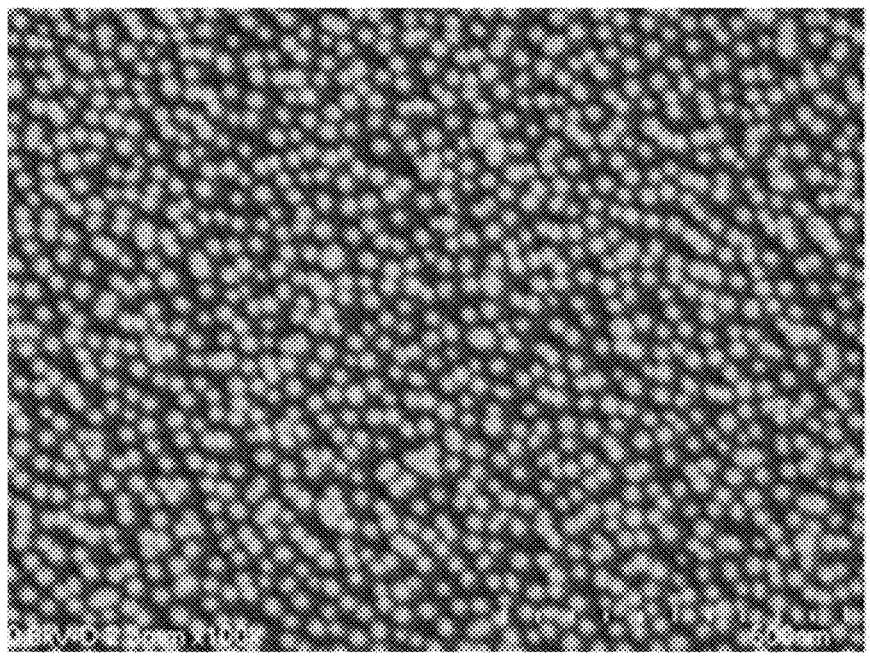
FIG. 3 is a view showing an example.

Example 1 was repeated, except that the gold plating step was repeated for 4 cycles to form a gold metal layer. This is shown in FIG. 3. The absorption spectrum curve is the third curve from the bottom in FIG. 6. It is obvious that the ratio $(S_A/S_B)$ of the geometric front area $(S_A)$ and back area $(S_B)$ exceeds 1. When observed after 7 days, crystals appeared.

As is clear from the results of Examples 1 to 7 and the comparative example described above, when the nanostructured substrate according to the present invention was impregnated with a biopolymer-containing solution, the biopolymer was crystallized. It is also found that biopolymer crystals are deposited in the nanostructured substrate according to the present invention by irradiation of electromagnetic waves. This indicates that biopolymer clusters are formed at many sites by electric field polarization, and that these crystal nuclei constitute a planar network and are crystallized. It can be easily understood that this biopolymer crystallization effect can be further enhanced by optimizing the irradiation conditions.

INDUSTRIAL APPLICABILITY

The biopolymer concentration method or crystallization method of the present invention is effective for the crystal growth of biopolymers. Further, the biopolymer concentration and crystal growth device of the present invention can be used for the detection of environmental hazardous substances, viruses, and the like. Moreover, the biopolymer concentration and crystal growth method etc. of the present invention are available for the industry of chemical and biological measurement, such as chemical sensors and biosensors.

The invention claimed is:

1. A biopolymer crystallization method for crystallizing a biopolymer by impregnating a nanostructured substrate with a biopolymer-containing solution while applying electromagnetic waves,
   wherein the nanostructured substrate comprises a base material, a base group fixed separately to the base material, and a metal layer group deposited on the base group, the base group is fixed separately to the base material, and
   a ratio $(S_A/S_B)$ of a geometric front area $(S_A)$ in terms of hemisphere on a total emission surface side of the metal layer group and a geometric back area $(S_B)$ on a total light-receiving surface side exceeds 1.

2. The biopolymer crystallization method according to claim 1, wherein the metal layer group has a peak-valley structure.

3. The biopolymer crystallization method according to claim 1, wherein the base group is a metal fine particle group.

4. The biopolymer crystallization method according to claim 1, wherein the metal layer group is composed of a reductively deposited metal or alloy.

5. The biopolymer crystallization method according to claim 1, wherein the metal layer group, or the metal layer group and the base group show plasmon characteristics.

6. The biopolymer crystallization method according to claim 1, wherein the biopolymer is a membrane protein.

\* \* \* \* \*